(12) United States Patent
Di Sarno

(10) Patent No.: US 10,379,073 B2
(45) Date of Patent: Aug. 13, 2019

(54) COMPOSITE-MATERIAL PRESSURE VESSEL AND SYSTEM AND METHOD FOR CONTROLLING THE VESSEL

(71) Applicant: Faber Industrie S.p.A., Cividale del Friuli, Udine (IT)

(72) Inventor: Raffaele Di Sarno, Cividale del Friuli (IT)

(73) Assignee: Faber Industrie S.p.A., Udine (IT)

( * ) Notice: Subject to any disclaimer, the term of this patent is extended or adjusted under 35 U.S.C. 154(b) by 303 days.

(21) Appl. No.: 15/129,673

(22) PCT Filed: Mar. 28, 2014

(86) PCT No.: PCT/IT2014/000086
§ 371 (c)(1),
(2) Date: Sep. 27, 2016

(87) PCT Pub. No.: WO2015/145468
PCT Pub. Date: Oct. 1, 2015

(65) Prior Publication Data
US 2017/0146477 A1    May 25, 2017

(51) Int. Cl.
*F17C 1/00* (2006.01)
*A62C 13/62* (2006.01)
(Continued)

(52) U.S. Cl.
CPC ............. *G01N 27/24* (2013.01); *A62C 13/62* (2013.01); *A62C 13/76* (2013.01); *A62C 37/50* (2013.01);
(Continued)

(58) Field of Classification Search
CPC ...... F17C 2203/0604; F17C 2203/0663; F17C 2203/0619; F17C 2250/0491; F17C 2260/036; F17C 13/025; G01N 27/24
See application file for complete search history.

(56) References Cited

U.S. PATENT DOCUMENTS 3,843,010 A * 10/1974 Morse ................. F17C 1/06
                                                        138/30
4,623,953 A * 11/1986 Dakin .................. H01G 4/221
                                                        174/17 LF
(Continued)

FOREIGN PATENT DOCUMENTS

DE        2114348 A1    10/1971
DE        2151137 A1    4/1973
(Continued)

*Primary Examiner* — David A Rogers
(74) *Attorney, Agent, or Firm* — Blank Rome LLP

(57) ABSTRACT

A composite-material pressure vessel (1) has a wall (4) with a reinforcing layer (11) containing one or more reinforcing fibers, wherein the reinforcing layer is an electrical conductor, wherein the wall (4) forms an electrical capacitor (13) having a first plate formed of the reinforcing layer (11), a second plate formed of an electrically conductive layer (15) overlapping the dielectric layer (11), a dielectric layer (14) interposed between the reinforcing layer (11) and the electrically conductive layer (15), as well as electrical terminals (19, 20) connected to the first and the second plates. The vessel control method and system perform electrical tests on the capacitor to derive information about the wall (4) structural condition.

15 Claims, 2 Drawing Sheets

(51) Int. Cl.
*A62C 13/76* (2006.01)
*A62C 37/50* (2006.01)
*G01N 27/24* (2006.01)
*G01R 31/02* (2006.01)

(52) U.S. Cl.
CPC .............. *F17C 1/00* (2013.01); *G01R 31/028* (2013.01); *F17C 2201/0104* (2013.01); *F17C 2201/056* (2013.01); *F17C 2201/058* (2013.01); *F17C 2203/066* (2013.01); *F17C 2203/0624* (2013.01); *F17C 2203/0663* (2013.01); *F17C 2223/0123* (2013.01); *F17C 2223/035* (2013.01); *F17C 2260/011* (2013.01); *F17C 2260/036* (2013.01); *F17C 2270/0168* (2013.01); *F17C 2270/02* (2013.01); *F17C 2270/05* (2013.01); *F17C 2270/0754* (2013.01)

(56) References Cited

U.S. PATENT DOCUMENTS

| | | | | |
|---|---|---|---|---|
| 4,699,288 A * | 10/1987 | Mohan | ................ | B29C 53/602 220/560.01 |
| 5,287,988 A * | 2/1994 | Murray | ................ | F16J 12/00 220/589 |
| 5,429,845 A * | 7/1995 | Newhouse | ................ | F17C 1/16 138/30 |
| 5,476,189 A * | 12/1995 | Duvall | ................ | F17C 1/16 220/588 |
| 5,522,428 A * | 6/1996 | Duvall | ................ | B60K 15/03006 137/624.11 |
| 5,822,838 A * | 10/1998 | Seal | ................ | B21D 51/24 29/469.5 |
| 5,829,418 A * | 11/1998 | Tamura | ................ | B60K 15/03006 123/529 |
| 6,662,632 B1 | 12/2003 | Parker et al. | | |
| 6,785,616 B2 * | 8/2004 | Lung | ................ | G01H 1/00 702/138 |
| 6,953,129 B2 * | 10/2005 | DeLay | ................ | F17C 1/06 220/562 |
| 7,526,961 B2 * | 5/2009 | Downie | ................ | F17C 13/025 73/718 |
| 7,687,764 B1 * | 3/2010 | Knapp | ................ | G01D 11/245 250/227.14 |
| 7,698,943 B2 * | 4/2010 | Bohse | ................ | G01N 29/14 702/82 |
| 9,383,281 B2 * | 7/2016 | Hashim | ................ | F17C 13/025 |
| 10,240,720 B2 * | 3/2019 | Cola | ................ | F17C 1/06 |
| 2004/0206762 A1 * | 10/2004 | Iida | ................ | B29C 53/8016 220/581 |
| 2006/0099366 A1 * | 5/2006 | Takemoto | ................ | B29C 70/088 428/36.1 |
| 2006/0291767 A1 * | 12/2006 | Andrews | ................ | G01M 11/085 385/13 |
| 2007/0113959 A1 * | 5/2007 | Minta | ................ | F17C 1/002 156/184 |
| 2010/0001851 A1 * | 1/2010 | Handa | ................ | F17C 1/16 340/438 |
| 2010/0206887 A1 | 8/2010 | Hashim et al. | | |
| 2012/0255948 A1 * | 10/2012 | Kanezaki | ................ | F17C 13/02 220/62.11 |
| 2012/0305107 A1 * | 12/2012 | Yahashi | ................ | B60K 15/07 137/456 |
| 2013/0299505 A1 * | 11/2013 | Otsubo | ................ | B29C 53/602 220/590 |
| 2016/0010802 A1 * | 1/2016 | Leavitt | ................ | F17C 13/003 250/459.1 |
| 2017/0292655 A1 * | 10/2017 | Glaesemann | ................ | G01D 7/005 |

FOREIGN PATENT DOCUMENTS

| | | |
|---|---|---|
| DE | 40 25 564 C1 | 9/1991 |
| DE | 10 2011 105 298 A1 | 12/2012 |
| EP | 0410503 A1 | 1/1991 |
| EP | 1128113 A1 | 8/2001 |
| FR | 2872904 A1 | 1/2006 |
| GB | 2 435 519 A | 8/2007 |
| WO | WO 2007/002266 A2 | 1/2007 |

* cited by examiner

COMPOSITE-MATERIAL PRESSURE VESSEL AND SYSTEM AND METHOD FOR CONTROLLING THE VESSEL

It is the object of the present invention a composite-material pressure vessel, e.g., a gas cylinder or a pressure accumulator, for storing pressurized gas.

The known composite-material gas cylinders usually comprise an inner layer, for example, made of steel or a synthetic material, ensuring the impermeability to the stored gas, and an outer layer in fibre-reinforced composite material ensuring the mechanical strength of the cylinder at the operating pressures, as well as a neck forming a passage opening from the outside to the inside of the cylinder, and a seat for receiving a valve for opening and closing the passage opening.

The known gas cylinders are intended for multiple uses, and the regulations for manufacturing and testing them vary depending on the application. Among the main applications for gas cylinders, storage of liquefied or compressed gases for motor propulsion, household or industrial uses, storage of compressed or liquefied gases for industrial use, buffer tanks for compressed air, storage of breathable mixtures for breathing apparatuses, storage of medical gases, and extinguishers may be mentioned.

By virtue of the use of different materials for the functions of impermeability and mechanical resistance to pressure, the composite gas cylinders have a weight/carrying capacity ratio that is very low and extremely interesting for applications in the automotive field.

However, the relatively complex structure of the composite gas cylinders, and the interaction between the different, materials of the impermeabilization layer, the reinforcing layer, and the neck may involve sealing problems of the cylinder and phenomena of degradation of the synthetic materials and the interface zones between the inner layer, the outer layer, and the neck, particularly in the case of prolonged operating times.

Such structural, and sealing degradation is worsened by the difference between the thermal expansion coefficients of the materials of the inner impermeabilization layer and the outer reinforcing layer (that are mutually connected over the entire surface), which involves a cyclic stress of the two layers, and by their interface, caused by the fact that a free and independent thermal deformation thereof is prevented.

Finally, the composite-material gas cylinders are sensitive to damages following mechanical impacts, cuts or abrasions that may damage the reinforcing fibre layer and reduce the stored gas pressure resistance.

In order to reduce or eliminate the risk of explosion of a composite gas cylinder, for example, in the automotive field, the need is felt to be able to reliably and easily perform a diagnosis of the possible damages.

To this aim, diagnosis systems have been proposed, by means of optical fibres wound in the reinforcing layer of the gas cylinder and connectable to a light source and a device for processing light pulses that are transmitted by the light source through the optical fibre. To date, such solution is not very reliable and it is very expensive, due to the cost of the optical fibre.

Furthermore, there are proposals to indicate a possible damage by means of dye capsules that are buried in the cylinder wall and so configured as to release the dye in the event of an impact, thus providing a visual indication of the damage suffered. However, this solution is not suitable for an automatic, systematic, and standardized diagnosis as required, e.g., for the automotive field.

Therefore, the object of the present invention is to provide a composite-material pressure vessel, having such characteristics as to obviate at least some of the drawbacks mentioned with reference to the prior art.

A particular object of the present invention is to provide a composite-material pressure vessel arranged to allow a diagnosis of the damages in a simple and reliable manner, with reduced costs, and automatically, for example, by the automatic or systematic processing of electric signals affected by the pressure vessel as a function of the structural condition thereof.

This and other objects are achieved by a composite-material pressure vessel having a wall defining an inner storage space, wherein said wall comprises:
 a reinforcing layer containing one or more reinforcing fibres, said reinforcing layer being an electrical conductor,
characterized in that it comprises an electrical capacitor having:
 a first plate formed of the reinforcing layer,
 a dielectric layer extending externally about the reinforcing layer,
 a second plate formed of an electrically conductive layer extending externally about the dielectric layer,
 electrical terminals connected to the first and the second plates.

By virtue of the configuration of the pressure vessel so that at least one structural component thereof forms an electric component of an electrical capacitor, it is possible to diagnose structural properties and, therefore, possible structural damages, of the component by means of electrical tests performed on the capacitor. The electrical tests, in turn, can be performed automatically at predetermined time intervals or as a function of predetermined events, for example, as a function of determinate operation steps of a gas-powered motor vehicle, and driven by an electronic control circuit.

The objects of the invention are also achieved by a method for verifying the structural integrity of a composite-material pressure vessel having a wall defining an inner storage space and comprising a reinforcing layer containing one or more reinforcing fibres, in which the method comprises:
 producing said reinforcing layer as an electrical conductor,
 producing a dielectric layer externally about the reinforcing layer,
 producing an electrically conductive layer externally about the dielectric layer,
so that the reinforcing layer, the dielectric layer, and the conductive layer form an electrical capacitor,
 subjecting the electrical capacitor to at least one electrical test to detect at least one electric characteristic of the capacitor,
 generating at least one datum representative of a structural property of the reinforcing layer depending on the detected electric characteristic.

In order to better understand the present invention and appreciate the advantages thereof, some exemplary, non-limiting embodiments thereof will be described herein below, with reference to the figures, in which.

Figure 1:
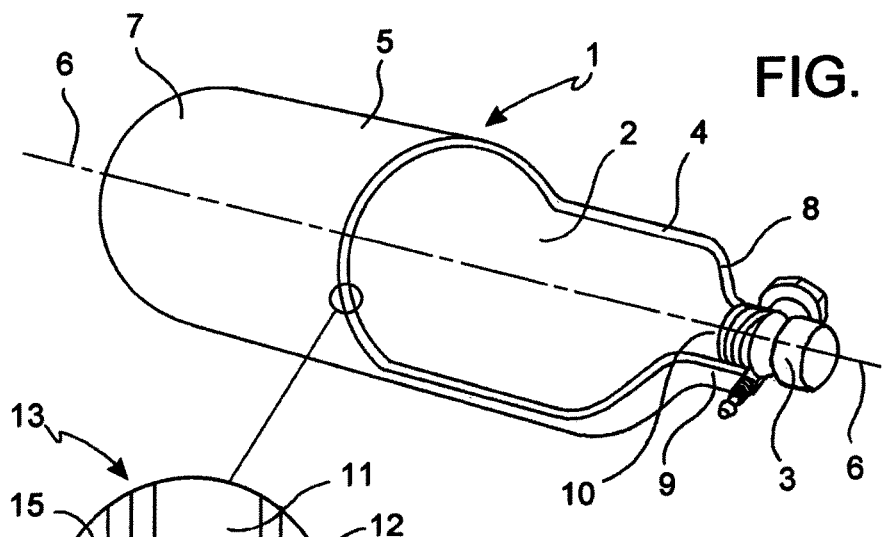
FIG. 1 is a longitudinal sectional view of a gas cylinder according to an embodiment of the invention.
Figure 2:
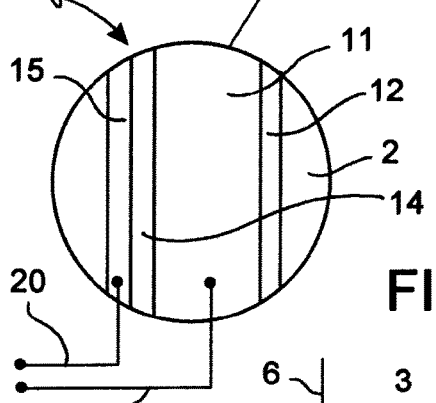
FIG. 2 is an enlarged view of a detail in FIG. 1.
Figure 4:
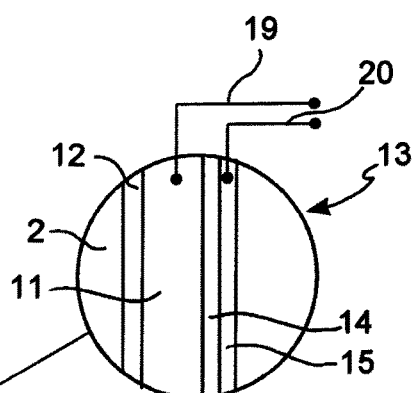
FIG. 4 is an enlarged view of a detail in FIG. 2.

With reference to the Figures, a gas cylinder (herein below "cylinder") or a pressure accumulator in general are indicated on the whole with the numeral reference 1 and represent non-limiting examples of a composite-material pressure vessel.

The cylinder 1 comprises a wall 4 defining internally a gas storage space 2 closable by a closing valve 3.

The wall 4 performs the function of resisting the inner pressure exerted by a stored gas or a different mechanical, thermal, or chemical stress.

The wall 4 may be rigid, and it forms in a broad sense a composite structural component at least one structural property of which is desired to be monitored and/or verified and/or tested and/or stored, e.g., a breaking strength, the absence/presence of damages, the structural integrity, the continuity of material and/or layer and/or fibre and/or surface, etc.

In accordance with an aspect of the invention, the wall 4 comprises:

a sealing layer 12 internally defining the gas storage space 2, a reinforcing layer 11 extending externally to (about the) sealing layer 12 and containing one or more reinforcing fibres, said reinforcing layer 11 being an electrical conductor, as well as an electrical capacitor 13.

The electrical capacitor 13 is formed of a first plate formed of the reinforcing layer 11, a dielectric layer 14 extending externally to (about the) reinforcing layer 11, a second plate formed of an electrically conductive layer 15 extending externally to (about the) dielectric layer 14, as well as electrical terminals 19, 20 connected to the first and the second plates.

By virtue of the configuration of the gas cylinder 1 so that at least one structural component thereof (the wall 4) forms an electric component of an electrical capacitor, it is possible to diagnose structural properties and, therefore, possible structural damages, of the component by electrical tests performed to the capacitor 13. The electrical tests, in turn, can be performed automatically at predetermined time intervals or as a function of predetermined events, for example as a function of determinate operation steps of a gas-powered motor vehicle, and driven by an electronic control circuit.

According to the invention, the method for monitoring the structural conditions of the gas cylinder 1 comprises the steps of subjecting the electrical capacitor 13 formed of the wall 4 to at least one electrical test to detect at least one electric characteristic of the capacitor, and generating at least one datum representative of a structural property of the reinforcing layer 11 depending on the detected electric characteristic.

The electrical test step of the capacitor 13 may comprise the detection of the capacitance of the capacitor. To this aim, an electric potential difference (voltage) is applied between the first and second plates (reinforcing layer 11 and electrically conductive layer 15) and the charge Q of the capacitor 13 is detected, which is proportional to the applied voltage, or a magnitude related thereto (for example, a discharge time constant of a measuring circuit of the R—C type comprising the capacitor 13). The electric capacitance [in farads] is the constant of proportionality in the ratio between the charge Q and the applied voltage (C=Q/Delta V) and forms an electric characteristic of that particular capacitor 13. The capacitance C depends on the geometries of the first and second plates and on the type, distribution, and thickness of the material in the dielectric layer 14. Consequently, the detected capacitance C depends, among the other characteristics, also on structural characteristics of the reinforcing layer, e.g., the thickness or changes in thickness, continuity, discontinuity, interruptions, cuts, lacerations, crushing, etc.

In addition or alternatively, the electrical test step of the capacitor 13 may comprise the detection of the absolute electric permittivity of the capacitor 13. In the simplest and non-limiting example, the capacitance C of a planar capacitor 13 with planar and parallel plates would be proportional to the ratio between the surface S of one of the first and second plates and the distance d thereof. The absolute electric permittivity ε [in farad/m] is the constant of proportionality of the ratio between the surface S, the distance d, and the capacitance C (C=ε*S/d) and forms an electric characteristic of the dielectric layer 14 interposed between the reinforcing layer 11 and the electrically conductive layer 15 that depends, among the other characteristics, also on structural characteristics of the multilayer wall 4, e.g., thickness or thickness changes, continuity, discontinuity, interruptions, cuts, lacerations, crushing, etc., of one or more of the layers 11, 14, 15.

Of course, for more complex geometrical shapes (cylinder, sphere, spherical cap, etc.), there are formulae for the calculation of the electric magnitudes of the capacitor 13 and known methods for an experimental detection thereof.

In addition or alternatively, the electrical test step of the capacitor 13 may comprise the detection of the impedance Z of the capacitor 13 at one or more predetermined frequencies, for example applying a sinusoidal voltage signal with known amplitude at the predetermined frequency and detecting the amplitude of the resulting sinusoidal electric current, and calculating the impedance of the capacitor 13 depending on the amplitudes of the applied voltage and the detected current. The impedance Z also constitutes an electric characteristic of the wall 4 that depends, among the other characteristics, also on its structural characteristics.

In accordance with an embodiment, the verification method comprises the steps of calculating and/or detecting one or more reference values of electric characteristics of the capacitor 13 of the intact wall 4, i.e., without damages or anomalies, storing the reference values, and, during a verification of the cylinder 1, comparing real values of the detected electric characteristics with the reference values and generating a datum representative of the structural condition of the wall 4 depending on the comparison between the real value and the reference value.

In this manner, it is possible to obtain, for example during a quality control of a new gas cylinder, or during a verification of structural integrity of a used gas cylinder, a datum or an electric signal containing, e.g., the piece of information:

"the verified cylinder is compliant with the reference values" or "the verified cylinder is not compliant with the reference values", "the verified used cylinder does not exhibit alterations" or "the verified used cylinder exhibits alterations".

In accordance with a further embodiment, the verification method comprises the steps of calculating and/or detecting one or more "anomaly indicating values" of electric characteristics of the capacitor 13 of the damaged wall 4 or the wall 4 with structural anomalies classified in advance, storing the anomaly indicating values, and, during a verification of the cylinder 1, comparing real values of the detected electric characteristics with the anomaly indicating values and generating the datum representative of the structural condition of the wall 4 depending on the comparison between the real value and the anomaly indicating value.

In this manner, it is possible to obtain, for example during a quality control of a new gas cylinder or during a verification of the structural integrity of a used gas cylinder, a datum or an electric signal containing, e.g., the piece of information:
"the verified cylinder exhibits an unclassifiable anomaly" or "the verified cylinder exhibits a classified anomaly [with the indication of the anomaly already classified]", For carrying out the verification of the wall 4 of the gas cylinder 1, an electronic control unit 16 can be provided for, with an electronic processor 17 and a memory 18, connected or connectable to the terminals 19, 20 of the capacitor 13 and configured to:
carry out the verification steps, and
process and store one or more of:
the reference values,
the anomaly indicating values,
the threshold intervals of the reference values indicative for the maximum allowable variations for the corresponding real values detected,
the real values detected, and/or
changes over time of the real values detected,
compare the detected real values with the reference values and/or with the anomaly indicating values and/or with the threshold intervals of the reference values, of the electrical magnitudes of the capacitor 13.

In accordance with an embodiment, the control and monitoring method of the pressure vessel comprises calculating the change of the real value of an electric magnitude detected during a control with respect to the real value of the same magnitude detected during a previous control (delta real value depending on a delta time) and using the calculated change of the real value to identify and, possibly, discard false diagnoses of anomalies actually due to the inevitable aging of the dielectric layer over time.

According to a still further embodiment of the invention, the method provides for detecting, and the control unit 6 can be configured to indirectly detect:
a pressure; and/or
a pressure change depending on the time; and/or
a geometrical magnitude (expansion, retraction) of the entire wall 4 or measured individual parts thereof; and/or
a history of loading/unloading cycles of the vessel, as well as an analysis of values derived from the cyclical curve of the stress of the pressure vessel 1, depending on the real values of the detected electrical magnitudes of the capacitor 13.

In fact, the method may use the proportionality between the pressurization state of the pressure vessel 1 and the thicknesses/distances of the layers composing the electrical capacitor 13 and determining the electric characteristics thereof.

In accordance with a further aspect of the invention, the control unit 6 is configured as one, or at least comprises one data storing unit that is tamper-proof or is protected against data deletion (a black box) to allow a later verification of possible causes of anomalies or incidents.

According to a further embodiment of the invention, the method provides for detecting, and the control unit 6 can be configured to detect real values of properties or electrical magnitudes of the individual components of the capacitor 13, for example, only of the reinforcing layer 11 or only of the electrically conductive layer 15, particularly, an electrical resistance thereof, and to carry out comparisons with corresponding reference values and/or anomaly indicating values and to generate signals or data representative for mechanical properties of the wall 4 similarly to what has been described above with reference to the electrical magnitudes of the capacitor 13.

In accordance with an embodiment, the control unit 16 is further connected to a notification device 21, for example, a display or an acoustic notification device, and configured to control the notification device 21 to emit a notification depending on a result of the performed verification of the wall 4.

The notification may be, for example, a confirmation of the structural integrity of the gas cylinder 1 or an alert notification in the case of an anomaly or an exhortation to carry out a repair or replacement of the gas cylinder 1, for example, in the case that the gas cylinder and the cylinder verification system are installed in a motor vehicle.

In accordance with a further embodiment, the control unit 16 is in signal communication, for example, wired or wireless, with a remote monitoring station 22 and configured to generate and transmit to the remote monitoring station 22 monitoring signals depending on a result of the performed verification of the wall 4.

The communication of possible anomalies to the remote monitoring station 22 allows a prompt intervention by third parties in the case that the user of the gas cylinder 1, for example a driver of a motor vehicle, should ignore an anomaly notification and would like to continue using the motor vehicle with a potentially defective gas cylinder 1.

According to a further embodiment, the control unit 16 can be further in signal connection with:
a sensor 25 configured to detect a value representative of the pressure in the inner space 2, for example a surface strain detecting sensor or a deformation of the wall 4, and/or
a sensor 26 configured to detect a value representative of the wall 4 temperature, and arranged or designed to store the detected temperature and pressure values, possibly as a chart of values defining a pressure curve as a function of time and/or a temperature curve as a function of time.

In this case, the control unit 6 can generate the control signal or datum of the structural condition of the wall 4 also depending on the pressure and/or temperature detected and possibly stored.

In an embodiment, the control unit 6 can be connected to an electrically conductive layer (for example, the fibre-containing reinforcing layer or, alternatively, a metal layer) of the gas cylinder 1 forming a capacitor and/or a different pressure vessel having only the electrically conductive layer and the dielectric layer (without per se forming both plates of a capacitor), and configured so as to detect a charge change in the electrically conductive layer (for example, due to a metal object approaching or more generally an object with an electrostatic charge approaching) of the capacitive "touch control" type, and to generate and possibly store a signal indicative of a possible tampering of the vessel.

In this embodiment of the method and the control device 6, the portion of the pressure vessel (electrically conductive layer, e.g., reinforcing layer, and dielectric layer, for example outer covering layer of the vessel) connected to the control unit 6 would form a capacitor only when a foreign body with an electrostatic charge would approach the dielectric covering layer.

This allows extending at least the aspect of the detection of possible tampering events even to known pressure vessels, optionally adapted to meet the above-described capacitive touch control configuration, of course, in combination with the method step and/or the control device described.

In accordance with an embodiment, the wall 4 may produce a plurality of capacitors 13 mutually (electrically) separate and formed in a plurality of different zones 24 of the wall 4. This allows carrying out the steps of verification of the structural integrity or the presence/absence of damages in a targeted manner for predetermined zones of the wall 4.

Figure 5:
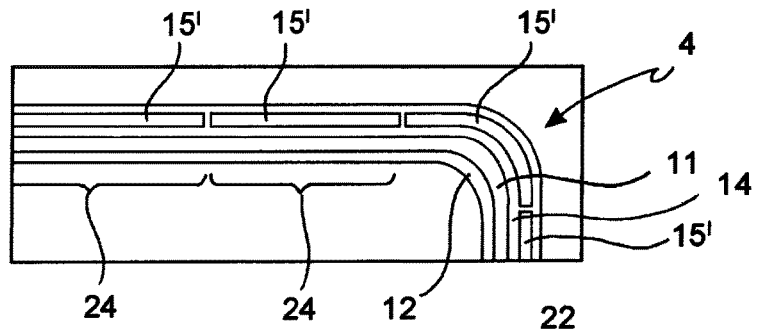
FIG. 5 is a sectional view of a detail of a composite-material structural component, for example, a gas cylinder or a pressure accumulator.
Figure 6:
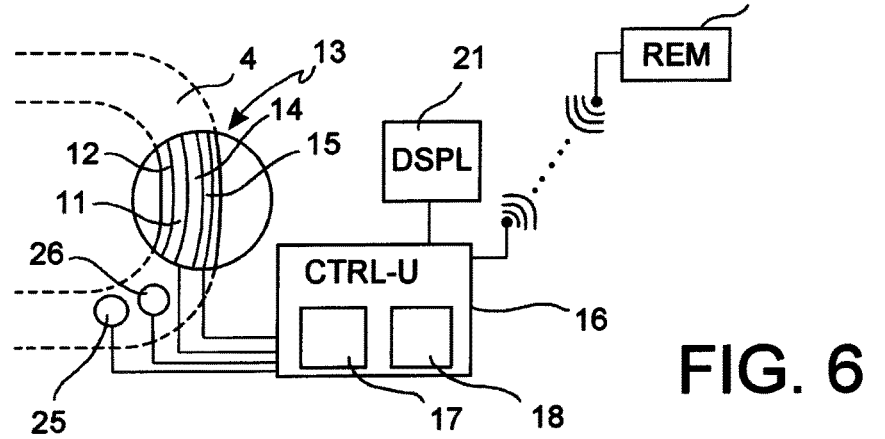
FIG. 6 shows a system for monitoring and diagnosing characteristics of a composite-material structural component, for example, a gas cylinder or a pressure accumulator.

In an embodiment (FIG. 5), the plurality of capacitors 13 is obtained by virtue of a separation of the electrically conductive layer 15 into a plurality of portions 15' that are mutually spaced apart and electrically insulated.

It shall be noticed that, in order to produce the one or more capacitors 13, the wall 4 of the cylinder 1 has to be configured so that the reinforcing layer 11 and the electrically conductive layer 15 are mutually spaced apart and electrically insulated.

The wall 4 geometry may vary depending on the application of the pressure vessel. In the example of a gas cylinder or a pressure accumulator, the wall 4 may have a tubular portion 5, preferably substantially cylindrical and extending along a longitudinal axis 6 of the cylinder 1, a bottom portion 7, for example, in the shape of a spherical or elliptical cap, connecting to a lower end of the tubular portion 5 and defining the inner space 2 on a lower side of the cylinder 1, as well as an upper portion 8, for example in an ogival shape, connecting to an upper end of the tubular portion 5 and defining the inner space 2 on an upper side of the cylinder 1 opposite the lower side.

Figure 3:
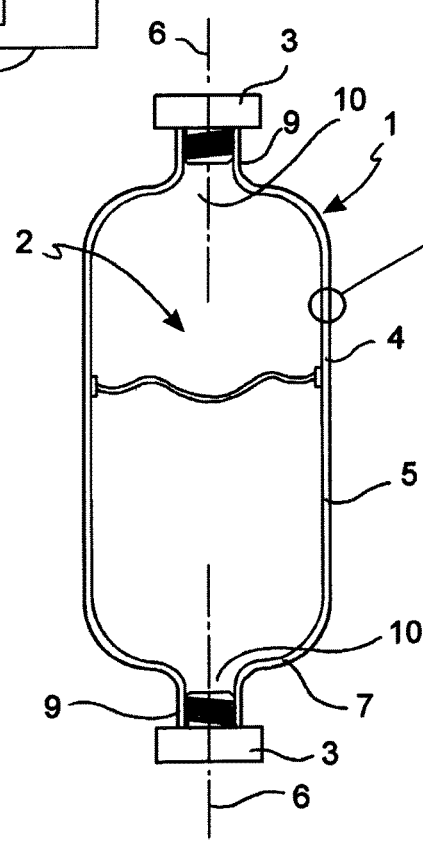
FIG. 3 is a longitudinal sectional view of a pressure accumulator according to an embodiment of the invention.

The cylinder 1 (FIG. 1) may further comprise a tubular neck 9 removably or irreversibly connected to an access opening 10 of the wall 4 and configured to receive the valve 3 in communication with the inner space 2. Sometimes the cylinder 1 may be configured as a pressure accumulator (FIG. 3) and a neck 9 with a valve 3 on both the opposite sides (upper portion 8, bottom portion 7) of the wall 4 can be provided for.

The reinforcing layer 11 may comprise carbon fibres, and it can be manufactured, for example by winding filaments of continuous carbon fibres impregnated with epoxy resin on a mandrel. The same mandrel can be then removed, for example by dissolution, mechanical crumbling or disassembling in the case of a mandrel in multiple pieces.

Alternatively, the mandrel about which the reinforcing layer 11 is wound remains integrated in the rigid wall 4 and forms a layer thereof, for example, an inner layer 12 ensuring the impermeability of the wall 4, or an intermediate layer (not shown) between the reinforcing layer 11 and the inner layer 12.

It is further contemplated that at least one of the reinforcing 11, dielectric 14, and electrically conductive 15 layers may be impermeable to the gas stored in the cylinder. In this manner, the wall 4 can be produced without the impermeable inner layer 12. In the applications where the wall 4 is not required to be impermeable, for example in gas cylinders or in pressure accumulators provided with a flexible and impermeable inner bag, and or in different structural applications, none of the layers of the wall 4 has to be necessarily gas-impermeable.

The reinforcing fibres of the reinforcing layer 11 may have a tensile strength above 4500 MPa, preferably from 4800 MPa to 5200 MPa, and an elastic module above 200 GPa, preferably from 200 to 250 GPa.

Advantageously, the reinforcing layer 11 comprises a (volumetric) content of reinforcing fibres ranging from 50% vol to 70% vol, preferably from 55% vol to 65% vol, still more preferably of about 60% vol, in which the rest of the volume is formed of matrix, which can be an epoxy resin or vinyl ester hardened by a thermal treatment, for example, by heating at about 120° for a duration of about 5 hours.

In accordance with an embodiment (type II pressure cylinders), the reinforcing layer 11, hence the conductive winding of the reinforcing carbon fibres occurs only in the tubular (or cylindrical) portion 5 of the wall 4, e.g., by a pure hoop-winding pattern and a thickness of the reinforcing layer 11, e.g., from 2 mm to 25 mm, depending on the design pressure. The axial load in this case is supported by the inner layer 12, e.g., a metal liner.

In accordance with a further embodiment (type III, IV pressure cylinders), the reinforcing layer 11, hence the conductive winding of the carbon reinforcing fibres occurs both in the tubular (or cylindrical) portion 5, and in the bottom 7 and upper 8 portions of the wall 4, e.g., by a pure hoop-winding pattern in the tubular portion and further helicoidal winding patterns covering also the bottom 7 and upper 8 portions.

The dielectric layer 14 can be composed of or comprise an insulating resin, e.g., an epoxy resin, polyester, or vinyl ester. Such a resin may form, for example, the matrix of the reinforcing layer 11 with carbon fibres and it may further form the dielectric layer 14 only of a resin with thicknesses that may generally range between 0.01 mm . . . 0.3 mm.

In order to obviate the difficulties in producing the dielectric layer 14 only of resin with a satisfactory thickness uniformity (in spite of the high area of the layers in the wall 4), it is advantageous to form the dielectric layer 14 with a mesh of dielectric synthetic material, e.g., polyester, buried in and/or filled with resin.

According to a further embodiment, the dielectric layer 14 comprises one or more sheets or webs of polyimide (Kapton®) or polyethylene terephthalate (Mylar®) bonded by one of the above-mentioned insulating resins.

According to a still further embodiment, the dielectric layer 14 comprises glass fibre, for example, wound about the reinforcing layer 11 and bonded by a matrix of epoxy resin, polyester, or vinyl ester. The systems for winding glass fibres to produce composite materials allow an accurate and reliable control of the dielectric layer 14 thickness, hence of the distance between the two plates of the capacitor 13.

The invention contemplates the use, in the dielectric layer 14, of high-strength S-type glass fibres, with 65% $SiO_2$, 25% $Al_2O_3$, 10% MgO, or E-type with 52-56% $SiO_2$, 12-16% $Al_2O_3$, 16-25% CaO, 8-13% $B_2O_3$.

The glass fibre in the dielectric layer 14 concurs, together with the carbon fibre reinforcement, also to the mechanical resistance of the pressure vessel 1, lowering the manufacturing costs thereof, but increasing its weight.

In accordance with embodiments, the electrically conductive layer 15 can be composed of or comprise:
  a conductive painting, for example, a paint with conductive adhesives such as (powder or granules of) graphite, copper, aluminum, etc.

a metal coating obtained by physical vapor deposition PVD or plasma-enhanced chemical vapor deposition PECVD a metal coating, obtained for example by metallic deposition by Thermal Arc Spray, Plasma Thermal Spray with various types of metals (Zinc, Aluminum, Zinc/Al alloys, . . . ).

The thickness of the electrically conductive layer 15 can be for example in the range from 0.01 mm to 0.5 mm and it has to ensure conductivity and possibly surface abrasion resistance.

The inner layer 12 (where applicable) may comprise a synthetic material (plastic liner), preferably thermoplastic, for example selected from the group comprising polyethylene, polyester, PET (polyethylene terephthalate), polyvinyl chloride, polytetrafluoroethylene. In accordance with an embodiment, the inner layer 12 comprises a fabric of natural or synthetic fibres or filaments, for example, polyester, which may be further coated or directly exposed in the inner space 2.

The inner layer 2 can be secured to the wall 4 by:

blow moulding in a mould composed of the reinforcing layer 11 with one or more possible intermediate layers, and/or moulding of the inner layer 12 (for example by a mould other than the reinforcing layer 11) and successive winding of the reinforcing layer 11 about the inner layer 12 and/or spraying and/or dip coating, which in the present case provides for a provisional filling of the inner space 2 with a coating liquid or with a coating powder that deposits the inner layer 2 on a semi-finished product of the wall 4.

Alternatively, the inner layer 12 (if provided) may comprise a metal material (metal liner).

Figure 7:
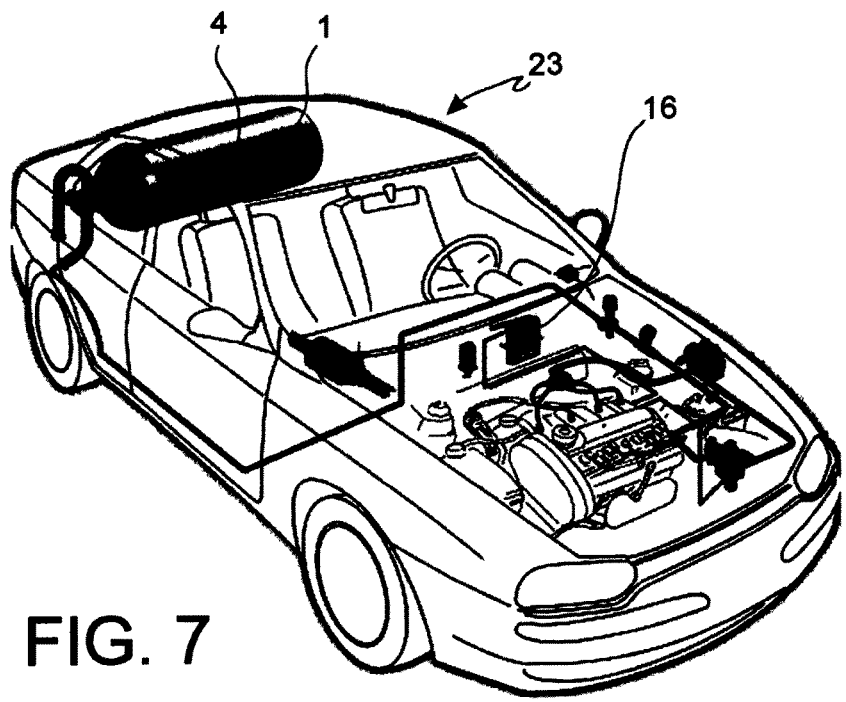
FIG. 7 shows a vehicle with a pressure tank, for example, a gas cylinder, and a system for monitoring and diagnosing structural characteristics of the tank according to an embodiment.

The gas cylinder 1, the verification or diagnosis system, and the verification method hereto described can be advantageously used for example in vehicles provided with pressure vessels, for example, gas-powered cars 23 (FIG. 7), industrial, civilian, and military plants, hospitals, as well as during a quality control step when manufacturing pressure vessels.

The order described for the reinforcing 11, dielectric 14, and electrically conductive 15 layers is particularly advantageous for gas cylinders of the II, III or IV type, but the references "externally" and "outer" or "internally" and "inner" are not necessarily binding, since in a particular form of a pressure vessel, the reinforcing layer 11 could be located "externally" to the dielectric 14 and electrically conductive 15 layers. Of course, it is requisite that the dielectric layer 14 is interposed between the reinforcing 11 and electrically conductive 15 layers.

Although the present invention has been described with reference to the example of a pressure vessel, it is expressly contemplated by the inventors that the structural integrity verification method and system described may be advantageously used also for and in combination with composite-material structural components other than pressure vessels, for example, for aeronautical, aerospace, or hydro-mechanical structural components (such as, e.g., aircraft wings, wind rotor wings, turbine blades, etc.).

The invention claimed is:

1. A method for controlling structural properties of a pressure vessel, comprising:

providing a composite-material pressure vessel having a wall defining an inner storage space, in which said wall comprises:

a reinforcing layer containing one or more reinforcing fibres, said reinforcing layer being an electrical conductor, an electrically conductive layer overlapping the reinforcing layer, and a dielectric layer interposed between the reinforcing layer and the electrically conductive layer, so as to form an electrical capacitor with a first plate formed of the reinforcing layer, a second plate formed of the electrically conductive layer, and the dielectric layer, electrical terminals connected to the first and second plates of the capacitor, connecting an electric control system to the terminals of the pressure vessel, carrying out, by the electric control system, the following steps:

subjecting the capacitor to at least one electrical test to detect a real value of at least one electric characteristic of the capacitor, and generating at least one control signal or datum representative of a structural condition of said wall depending on the real value of the detected electric characteristic.

2. The method according to claim 1, comprising carrying out said electrical test automatically at predetermined time intervals or as a function of predetermined events.

3. The method according to claim 2, wherein the electrical test comprises one of:

detecting the capacitance of the capacitor, detecting the absolute electric permittivity of the capacitor, detecting the impedance of the capacitor at one or more predetermined frequencies.

4. The method according to claim 3, comprising:

calculating and/or detecting one or more reference values of electric characteristics of the capacitor of the intact wall, storing the calculated or detected reference values, comparing, by the electric control system, said real values of the detected electric characteristics to said stored reference values, generating said control datum or signal depending on a result of the comparison between the real value and the reference value.

5. The method according to claim 4, comprising:

calculating and/or detecting one or more anomaly indicating values, said anomaly indicating values being values of electric characteristics of the capacitor of the wall damaged or with structural anomalies classified in advance, storing the calculated or detected anomaly indicating values, comparing, by the electric control system, said real values of the detected electric characteristics with said stored anomaly indicating values, generating said control datum or signal depending on the results of the comparison between the real value and the anomaly indicating values.

6. The method according to claim 5, comprising the step of emitting, by the electric control system, a visual or acoustic notification depending on the generated control datum or signal.

7. The method according to claim 6, comprising the step of transmitting, by the electric control system, the control signal or datum to a remote monitoring station.

8. The method according to claim 7, wherein the steps of the method are carried out selectively for predetermined zones of the wall.

9. The method according to claim 8, comprising detecting a charge change in the electrically conductive layer due to an object with an electrostatic charge approaching the wall and generating a signal indicative of a possible tampering of the vessel.

10. The method according to claim 1, wherein the wall forms a plurality of said capacitors electrically separated from each other and located in a plurality of different zones of the wall.

11. The method according to claim 10, wherein the plurality of capacitors is obtained by subdivision of the electrically conductive layer into a plurality of mutually spaced apart and electrically insulated portions.

12. The method according to claim 1, wherein the reinforcing layer comprises resin-impregnated electrically conductive carbon fibers.

13. The method according to claim 1, wherein the dielectric layer comprises a mesh of dielectric synthetic material filled with insulating resin.

14. The method according to claim 1, wherein the dielectric layer comprises glass fiber bonded by an insulating resin matrix.

15. The method according to claim 1, wherein the electrically conductive layer comprises one of:
    a paint with conductive adhesives, or
    a metal coating obtained by physical vapor deposition PVD, or
    a metal coating obtained by plasma-enhanced chemical vapor deposition PECVD, or
    a metal coating obtained by spraying.

* * * * *